United States Patent
Walsdorff et al.

(10) Patent No.: US 6,518,220 B2
(45) Date of Patent: Feb. 11, 2003

(54) SHAPED CATALYSTS

(75) Inventors: Christian Walsdorff, Ludwigshafen (DE); Otto Hofstadt, Speyer (DE); Raimund Felder, Neustadt (DE); Ruprecht Meissner, Weisenheim (DE); Klaus Harth, Altleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/782,307

(22) Filed: Feb. 14, 2001

(65) Prior Publication Data

US 2001/0029235 A1 Oct. 11, 2001

(30) Foreign Application Priority Data

Feb. 25, 2000 (DE) .......................................... 100 09 017

(51) Int. Cl.[7] .............................. B01J 23/70; B01J 23/02; B01J 27/122; B29D 22/00; B32B 1/08
(52) U.S. Cl. ..................... 502/346; 502/344; 502/345; 502/225; 502/439; 502/527.14; 502/527.16; 502/527.17; 428/34.1; 428/36.92
(58) Field of Search ............................ 502/439, 527.14, 502/527.16, 527.24, 527.19, 344–346, 225; 428/34.1, 36.92

(56) References Cited

U.S. PATENT DOCUMENTS

| | | | | |
|---|---|---|---|---|
| 2,408,162 A | * | 9/1946 | Foster ..................... 252/259.2 |
| 3,893,952 A | * | 7/1975 | Ryska et al. ............. 252/445 R |
| 4,260,524 A | * | 4/1981 | Yamada et al. .......... 502/527.14 |
| 4,282,116 A | * | 8/1981 | Reuter et al. ........... 502/527.16 |
| 4,366,093 A | * | 12/1982 | Shiozaki et al. ........ 502/527.16 |
| 4,441,990 A | * | 4/1984 | Huang ........................ 208/111 |
| 4,460,699 A | * | 7/1984 | Convers et al. ................ 502/84 |
| 4,656,157 A | * | 4/1987 | Hofmann et al. ....... 502/527.16 |
| 4,656,158 A | | 4/1987 | Matsuo et al. ................ 514/12 |
| 5,099,085 A | * | 3/1992 | Strasser et al. .............. 570/245 |
| 5,166,120 A | | 11/1992 | Deller et al. ................. 502/225 |
| 5,861,353 A | * | 1/1999 | Viola et al. .................. 502/225 |
| 5,905,054 A | * | 5/1999 | Cavalli et al. .............. 502/225 |

FOREIGN PATENT DOCUMENTS

| | | |
|---|---|---|
| EP | 017 865 | 10/1980 |
| EP | 184 790 | 6/1986 |
| EP | 0 184 790 | 6/1986 |
| EP | 461 431 | 12/1991 |
| EP | 1052018 | 11/2000 |
| EP | 1 052 018 | 11/2000 |
| GB | 893987 | 9/1959 |
| WO | WO99/19065 | 4/1999 |
| WO | WO 99/48606 | 9/1999 |

* cited by examiner

Primary Examiner—Mark L. Bell
Assistant Examiner—Patricia L. Hailey
(74) Attorney, Agent, or Firm—Keil & Weinkauf

(57) ABSTRACT

Shaped catalysts for heterogeneously catalyzed reactions are in the form of hollow cylinders or annular tablets whose end faces are rounded both to the outer edge and to the edge of the central hole, i.e. have no right-angled edges.

4 Claims, 3 Drawing Sheets a: outer edge
b: edge of central hole
c: end faces
d: radius of curvature of the end faces a: outer edge
b: edge of central hole
c: end faces
d: radius of curvature of the end faces

SHAPED CATALYSTS

The present invention relates to novel shaped catalysts for heterogeneously catalyzed reactions in the form of hollow cylinders or annular tablets whose end faces are rounded both to the outer edge and to the edge of the central hole, so that they have no right-angled edges EP-A-184 790 discloses shaped catalysts for heterogeneously catalyzed reactions in the form of a hollow cylinder which have curved "end faces" at the outer edge of the cylinder.

WO-A-99/48606 discloses catalysts in the form of annular tablets having dimensions of 5 mm×5 mm×2 mm (height x diameter x diameter of the central hole).

However, these catalysts leave something to be desired. In particular, the pressure drop over a bed of these catalysts is not yet optimal.

It is an object of the present invention to provide shaped catalysts for heterogeneously catalyzed reactions having improved properties, in particular a reduced pressure drop.

We have found that this object is achieved by new and improved catalysts for heterogeneously catalyzed reactions in the form of hollow cylinders or annular tablets whose end faces are rounded both to the outer edge and to the edge of the central hole (FIG. 1).

The catalysts of the present invention are produced by methods known per se, for example by precipitation of the oxides, hydrated oxides, hydroxides or other sparingly soluble compounds of the components from solutions of their salts, or by intensive mixing of the oxidic and/or salt-like starting materials, which may be dissolved and/or suspended in water or organic solvents, subsequent drying and, if appropriate, thermal decomposition of the salts, milling to a suitable tabletable particle size, shaping to the shape according to the present invention in suitable tableting machines and, if appropriate, subsequent thermal treatment at elevated temperatures in an oxidizing, reducing or inert atmosphere. Shaping aids such as graphite, carbon black, stearic acid, starch, polyacrylic acid, mineral oil, vegetable oil, methylcellulose, etc., and also reinforcing materials such as inorganic fibers, for example glass fibers or the like, or inorganic powders, for example metal powders, metal flocs, inert support materials, e.g. $SiO_2$, metal silicates and aluminum silicates, aluminum oxides, aluminum hydroxides, hydrated aluminum oxides, MgO, $TiO_2$, $ZrO_2$, $Nb_2O_3$, pumice, silicon carbide and/or magnesium silicates, can be added to the catalyst composition at any point during shaping.

The shaped catalysts of the present invention for heterogeneously catalyzed reactions are in the form of hollow cylinders or annular tablets of catalytically active material or preferably comprise inert support material which has been shaped into hollow cylinders or annular tablets and on which a catalytically active composition has been applied, where the external diameter of the hollow cylinders or annular tablets is from 3 to 20 mm, preferably from 3 to 10 mm, particularly preferably from 3 to 7 mm, in particular from 3.5 to 6.5 mm, with an internal diameter which is from 0.1 to 0.7 times the external diameter, and a length which is from 0.2 to 2 times, preferably from 0.3 to 1.8 times, particularly preferably from 0.4 to 1.6 times, the external diameter, and the radius of curvature of the end faces is from 0.01 to 0.5 times, preferably from 0.05 to 0.4 times, particularly preferably from 0.1 to 0.2 times, the external diameter.

Figure 1:
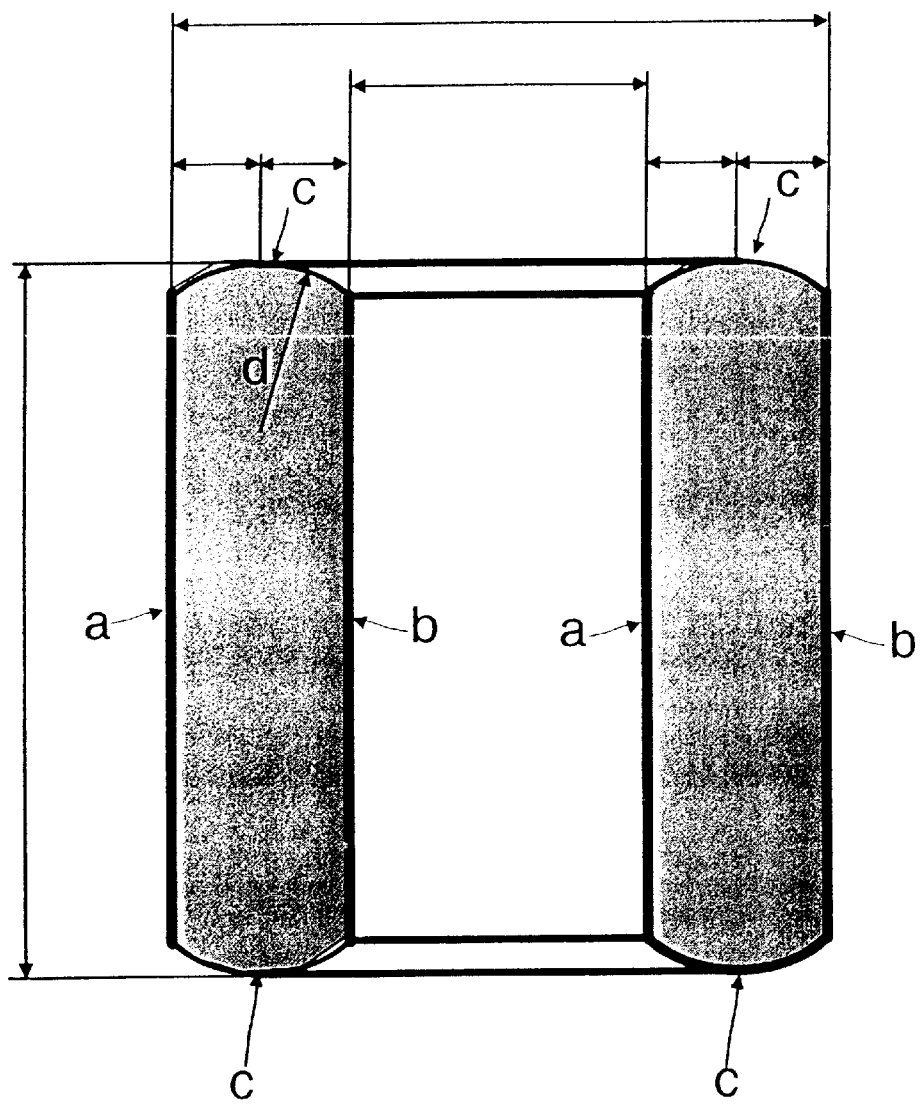
FIG. 1 illustrates a possible cross section of the shaped catalysts of the present invention.

The novel catalyst shape is also advantageous in the case of supported catalysts which are produced by applying the active components to the preshaped inert support by impregnation with, vapor deposition of or spraying-on of a solution or suspension of the components in the oxidic or salt form.

There are no restrictions in respect of the chemical composition of the catalysts.

The shaped catalysts of the present invention are suitable for heterogeneously catalyzed reactions in which they are used, for example, as fixed beds in gas-phase or liquid-phase reactions, in particular in strongly exothermic gas-phase reactions such as the oxychlorination of ethylene to form 1,2-dichloroethane.

The shaped catalysts of the present invention are preferably used for oxychlorination, in particular of ethylene to 1,2-dichloroethane. The composition of catalysts suitable for oxychlorination is based on a support, which preferably comprises a high-surface-area aluminum oxide such as γ- or δ-$Al_2O_3$. The BET surface area is generally in the range from 100 to 250 $m^2/g$, preferably from 150 to 220 $m^2/g$. Preferably, the support is, in a first step, shaped to the desired catalyst geometry by tableting, and active components are applied to the shape support in a subsequent step. In the starting material used for tableting the support, the high-surface-area aluminum oxide may be replaced completely or partly by other compounds such as pseudoboehmite which can be converted by calcination into a high-surface-area aluminum oxide. In addition, tableting aids such as graphite or magnesium stearate can also be added to the starting material to be tableted. Preference is given to using tableting mixtures as described in WO-A 99/48606.

According to the present invention, the material is tableted to form hollow cylinders or annular tablets. The hollow cylinders or rings generally have an arithmetic mean height of from 3 to 7 mm, preferably from 4.8 to 5.2 mm, particularly preferably from 4.9 to 5.1 mm, an arithmetic mean diameter of from 3 to 7 mm, preferably from 4.8 to 5.2 mm, particularly preferably from 4.9 to 5.1 mm, and an arithmetic mean diameter of the central hole of from 2 to 3.5 mm, preferably from 2.3 to 2.7 mm, particularly preferably from 2.4 to 2.6 mm.

After tableting, the catalyst supports are generally calcined. Calcination is generally carried out at from 500 to 800° C., preferably from 700 to 750° C. Calcination is generally performed in an oxidizing atmosphere, generally in air.

The tableting process described and the choice of starting materials generally gives a catalyst support which has both a good mechanical stability and a pore volume advantageous for oxychlorination. The catalyst supports for the oxychlorination which are obtained according to the present invention generally have a pore volume of from 0.1 to 0.9 $cm^3/g$, preferably from 0.3 to 0.7 $cm^3/g$, particularly preferably from 0.4 to 0.6 $cm^3/g$ and a lateral compressive strength of at least 20 N, preferably from 22 to 80 N, particularly preferably from 25 to 60 N, in particular from 27 to 55 N.

The supports obtained in this way can subsequently be impregnated with a solution of CuCl$_2$ and, if desired, further compounds such as KCl, other salts of alkali metals, alkaline earth metals or rare earth metals. If desired, hydrochloric acid can also be added to such a solution.

The volume of the impregnation solution is advantageously chosen so that it corresponds to from 10 to 200% of the pore volume of the support, preferably from 30 to 150%, particularly preferably from 90 to 110%.

After impregnation, the shaped catalyst bodies are generally dried at from 80 to 300° C., preferably from 100 to 200° C.

The concentration and the volume of the impregnation solution are chosen so that the supported catalyst generally has a Cu content of from 1 to 15% by weight, preferably from 2 to 10% by weight, and a K content of from 0.1 to 8% by weight, preferably from 0.3 to 3% by weight. The activity profile of the catalyst composition can be set as desired by selection of the metal concentrations in the catalyst and, if desired, by dilution with inert material such as Al$_2$O$_3$. The supported catalyst obtainable in this way is suitable for preparing 1,2-dichloroethane by oxychorination. It combines a low pressure drop with good mechanical strength.

The total pore volume (Hg porosimetry) of the catalyst supports of the present invention is at least 0.35 ml/g, preferably at least 0.4 ml/g, and the proportion of macropores is at least 10%, preferably from 15 to 50%, particularly preferably from 20 to 40%, over the total pore volume.

The novel shaped catalysts are suitable preferably for the oxychlorination of ethylene and, as a rule, also for other heterogeneously catalyzed reactions, for example for the preparation of acrylic acid, phthalic anhydride and maleic anhydride or the dehydrogenation of alkanes to alkenes, for example propane to propene. The preparation of catalysts shaped according to the invention which are intended for such and further reactions can be carried out analogously to the preparation of other catalysts suitable for this reaction, apart from the shaping according to the invention. These catalysts may be supported catalysts or unsupported catalysts.

EXAMPLE E1

Figure 2:
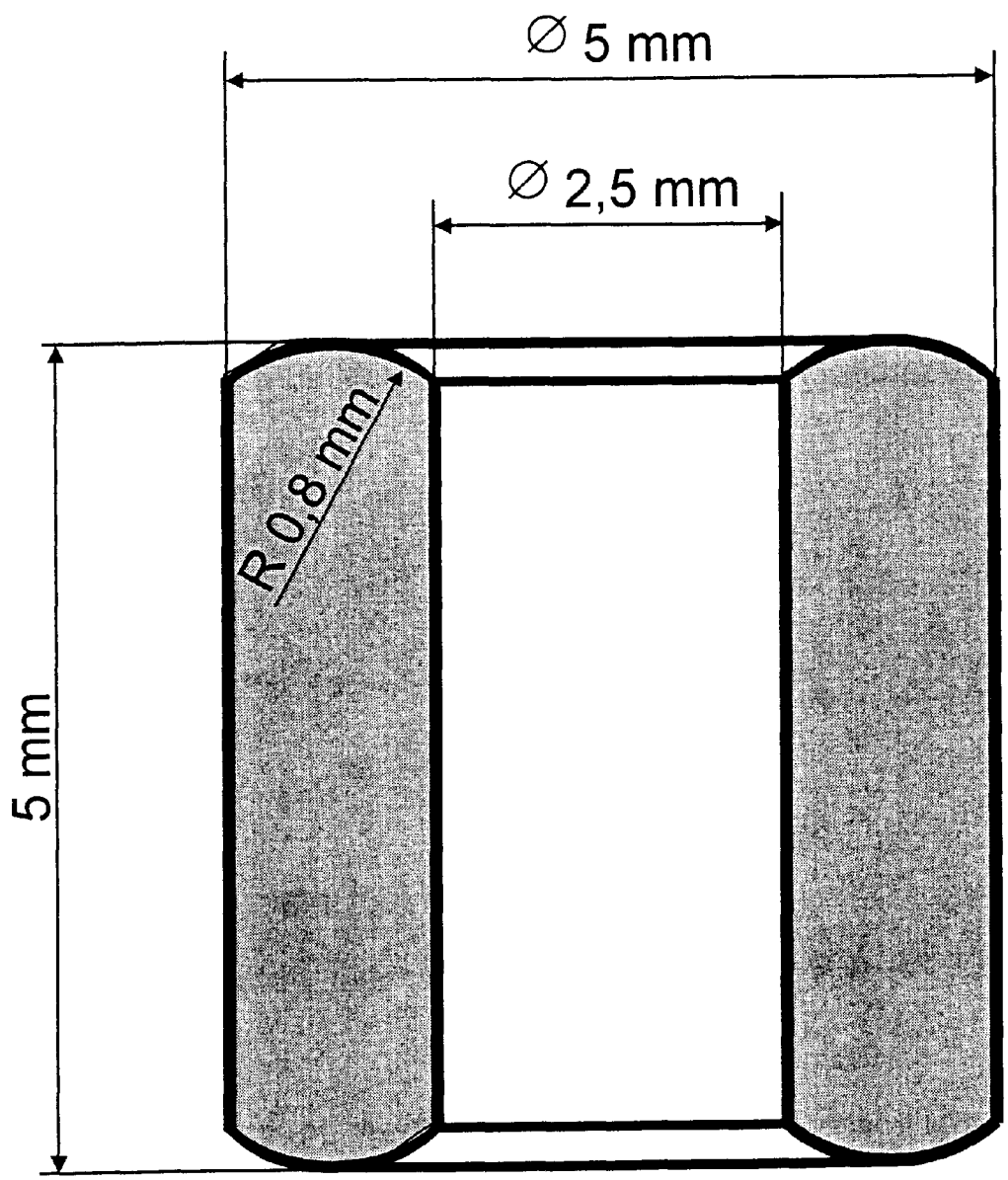
FIG. 2 illustrates a cross section of a shaped catalyst according to the present invention, having dimensions of 5 mm×5mm×2.5 mm (height x diameter x diameter of the central hole) and end faces rounded to the outer edge and to the edge of the central hole.

A dry mixture as described in WO 99/48606 was tabletted to form annular tablets having dimensions of 5 mm×5 mm×2.5 mm (height×diameter×diameter of the central hole) and end faces rounded to the outer edge and to the edge of the central hole as shown in FIG. 2 and having a lateral compressive strength of 20 N, and these were subsequently calcined at 700° C. for two hours. The physical data of the support are shown in Table 1.

EXAMPLE E1*

The support E1 was impregnated with a solution of copper chloride and potassium chloride to a copper content of 5.8% and a potassium content of 2.6%. For this purpose, a solution of copper chloride and potassium chloride having a volume corresponding to the water absorption was poured onto the supports, and the impregnated catalysts were dried at 120° C.

COMPARATIVE EXAMPLE C1

The same dry mixture as in E1 was, as described in WO 99/48606, tabletted to form annular tablets having dimensions of 5 mm×5 mm×2 mm (height x diameter x diameter of the central hole) and these were calcined.

EXAMPLE C1*

The support C1 was impregnated with a solution of copper chloride and potassium chloride to a copper content of 5.8% and a potassium content of 2.6%. For this purpose, a solution of copper chloride and potassium chloride having a volume corresponding to the water absorption was poured onto the supports, and the impregnated catalysts were dried at 120° C.

COMPARATIVE EXAMPLE C2

The same dry mixture as in E1 was tabletted to form annular tablets having dimensions of 5 mm×5 mm×2.5 mm (height×diameter×diameter of the central hole) and a lateral compressive strength of 20 N, and these were subsequently calcined at 700° C. for two hours.

COMPARATIVE EXAMPLE C3

Figure 3:
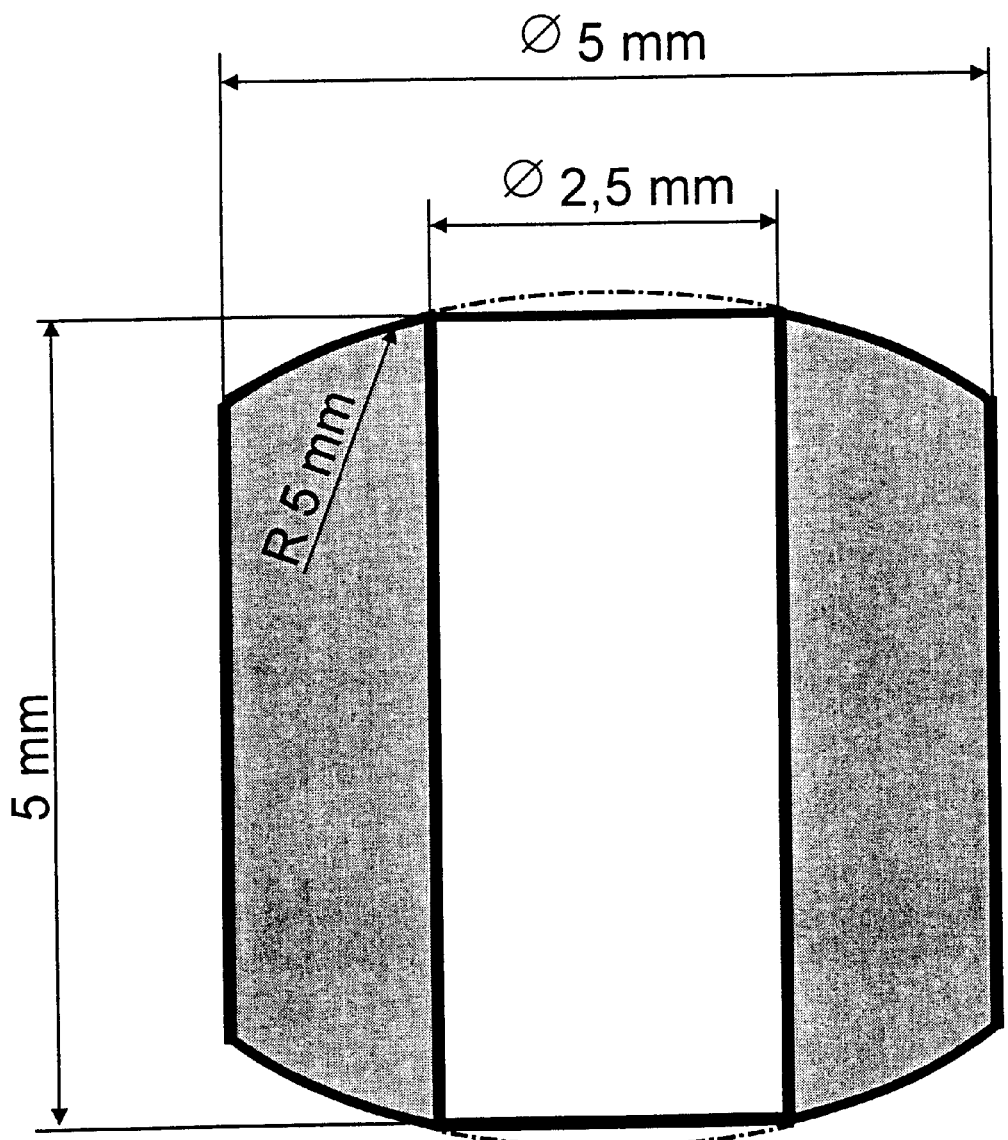
FIG. 3 illustrates a cross section of a shaped catalyst prepared as comparative example C3, having dimensions of 5 mm×5mm×2.5 mm (height x diameter x diameter of the central hole).

The same dry mixture as in E1 was tabletted form annular tablets having dimensions of 5 mm×5 mm×2.5 mm (height× diameter×diameter of the central hole) and rounded end faces corresponding to FIG. 3 and having a lateral compressive strength of 20 N, and these were calcined.

Pressure Drop Measurements

The pressure drop measurements were carried out on a bed having a length of one meter in a glass tube having a diameter of 2.5 cm. A diameter of the order of 2.5 cm is typical for the reactor tubes of industrial shell-and-tube reactors for strong exothermic heterogeneously catalyzed gas-phase reactions such as the oxychlorination of ethylene to ethylene dichloride. To obtain bits which are as homogeneous as possible and thus readily reproducible values, the supports were in each case added via a funnel so slowly that the supports fell on top of one another in succession and virtually individually.

Performance Tests

The catalysts from Example E1* and Comparative Example C1* were tested in a circulation reactor at a throughput of 1 mol of HCl/90 ml of catalyst and using a stoichiometric feed consisting of hydrogen chloride, ethylene and air. Table 3 shows the ethylene conversion and the combustion selectivity.

TABLE 1

Physical data of the supports

| | Lateral compressive strength [N] | Pore volume [ml/g] | BET surface area [m$^2$/g] | Water absorption [ml/g] |
|---|---|---|---|---|
| Example E1 | 25 | 0.42 | 160 | 0.48 |
| Comparative Example C1 | 31 | 0.43 | 197 | 0.52 |
| Comparative Example C2 | 24 | 0.41 | 177 | 0.50 |
| Comparative Example C3 | 25 | 0.41 | 170 | 0.51 |

TABLE 2

Relative pressure drop over a 1 m bed at a tube diameter of 2.5 cm

| $N_2$ flow [standard $m^3/h$], 2 bar | Comparative Example C1 weight of bed: 303.4 g Δp [mm $H_2O$] | Comparative Example C3 weight of bed: 280.6 g Δp [mm $H_2O$] | Comparative Example C2 weight of bed: 280.9 g Δp [mm $H_2O$] | Example E1 weight of bed: 284 g Δp [mm $H_2O$] | Relative pressure drop |
|---|---|---|---|---|---|
| 1.138 | 122 | 116 | 112 | 104 | 1:0.95:0.92:0.85 |
| 1.834 | 366 | 346 | 335 | 308 | 1:0.95:0.92:0.85 |
| 2.711 | 736 | 705 | 679 | 625 | 1:0.95:0.92:0.85 |

TABLE 3

Performance of the catalysts according to the present invention and the comparative catalysts

| | Temperature [° C.] | Conversion [%] of ethylene | Combustion selectivity [%] to CO + $CO_2$ | Selectivity [%] to chlorinated by-products |
|---|---|---|---|---|
| Example E1* | 240 | 70 | 0.46 | 1.39 |
| Comparative Example C1* | 240 | 72.7 | 0.69 | 1.49 |
| Example E1* | 270 | 79.6 | 2.65 | 4.72 |
| Comparative Example C1* | 270 | 78.7 | 3.1 | 4.83 |

The pressure drop of the shaped catalysts of the present invention is about 15% below that of the catalyst described in WO-A-99/48606 in the form of 5 mm×5 mm×2 mm annular tablets (Comparative Example C1). Compared to the support geometries of Comparative Examples C2 and C3, the novel shape of the support from Example E1 also displays a significantly reduced pressure drop, namely 11% lower and 8% lower, respectively. The support C2 is an improvement, in respect of pressure drop, of the support C1 which will be obvious to a person skilled in the art on the basis of the description in WO-A 99/48606. C3 is a modification of the support C2 in accordance with the teachings of EP-A-184 790. Since all the supports compared have virtually identical external dimensions and were studied at the same tube diameter typical of industrial reactor tubes, these results very clearly show the improved pressure drop of catalysts having the shape according to the present invention.

The advantage of the support geometry according to the present invention for the performance of corresponding catalysts in oxychlorination is shown by comparison of catalysts C1* and E1*. The catalyst having the shape according to the present invention (E1*) displays, at approximately the same conversion, a significantly improved selectivity compared to the catalyst having the known shape (C1).

We claim:

1. A shaped catalyst for heterogeneously catalyzed reactions in the form of hollow cylinders or annular tablets wherein in cross section the outer wall (outer boundary) and the inner wall (boundary of the central hole) are largely flat and parallel to one another, while the end faces are rounded over their entire area so that, viewed along the central hole, the catalyst body tapers both to the outer boundary and to the boundary of the central hole.

2. A shaped catalyst for heterogeneously catalyzed reactions as claimed in claim 1, produced by impregnating a shaped y-$Al_2O_3$ support having a BET surface area of from 100 to 250 g/$m^2$ with a solution comprising salts of copper.

3. A shaped catalyst for heterogeneously catalyzed reactions as claimed in claim 2, wherein the elements applied by impregnation are present in the form of their chlorides.

4. A process for producing a shaped catalyst for heterogeneously catalyzed reactions as claimed in claim 1, which comprises treating shaped y-$Al_2O_3$ supports having a BET surface area of from 100 to 250 g/$m^2$ with solutions comprising salts of copper and potassium.

* * * * *